United States Patent
Roller et al.

(10) Patent No.: US 10,285,801 B2
(45) Date of Patent: *May 14, 2019

(54) ADJUSTABLE SUTURE-BUTTON CONSTRUCT FOR KNOTLESS STABILIZATION OF CRANIAL CRUCIATE DEFICIENT LIGAMENT STIFLE

(71) Applicant: ARTHREX, INC., Naples, FL (US)

(72) Inventors: Brandon L. Roller, Naples, FL (US);
Eric S. Zajac, Naples, FL (US);
Ricardo Albertorio, Naples, FL (US);
James L. Cook, Birmingham, AL (US)

(73) Assignee: ARTHREX, INC., Naples, FL (US)

( * ) Notice: Subject to any disclaimer, the term of this patent is extended or adjusted under 35 U.S.C. 154(b) by 342 days.

This patent is subject to a terminal disclaimer.

(21) Appl. No.: 15/228,242

(22) Filed: Aug. 4, 2016

(65) Prior Publication Data

US 2016/0354197 A1 Dec. 8, 2016

Related U.S. Application Data

(60) Continuation of application No. 14/089,097, filed on Nov. 25, 2013, now Pat. No. 9,421,086, which is a
(Continued)

(51) Int. Cl.
*A61B 17/04* (2006.01)
*A61F 2/08* (2006.01)
*A61B 17/06* (2006.01)

(52) U.S. Cl.
CPC ........ *A61F 2/0811* (2013.01); *A61B 17/0401* (2013.01); *A61B 17/0487* (2013.01);
(Continued)

(58) Field of Classification Search
CPC ............ A61B 17/0401; A61B 17/0482; A61B 17/0487; A61B 17/06166;
(Continued)

(56) References Cited

U.S. PATENT DOCUMENTS 3,176,316 A 4/1965 Bodell
3,718,947 A * 3/1973 Huber ...................... B66C 1/14
24/298
(Continued)

FOREIGN PATENT DOCUMENTS

DE 29910202 U1 9/1999
DE 20101791 U1 6/2001
(Continued)

*Primary Examiner* — Dianne Dornbusch
(74) *Attorney, Agent, or Firm* — Carlson, Gaskey & Olds (57) ABSTRACT

An adjustable, knotless button/loop/needle construct for fixation of cranial cruciate ligament deficient stifle. The adjustable, knotless construct includes two fixation devices (for example, two buttons) and at least one flexible, adjustable loop attached to at least one of the fixation devices (e.g., the buttons). Preferably, a needle is attached to each of the fixation devices (e.g., the buttons). The adjustable, knotless construct has an adjustable loop length and allows adjustment in one direction while preventing or locking the construct from loosening in the opposite direction, due to applied tensile forces. The construct and technique of the present invention provides an improved knotless system for cruciate ligament repair.

19 Claims, 7 Drawing Sheets

Related U.S. Application Data division of application No. 13/298,912, filed on Nov. 17, 2011, now Pat. No. 8,628,573, application No. 15/228,242, which is a continuation-in-part of application No. 12/751,835, filed on Mar. 31, 2010, now Pat. No. 8,460,379, and a continuation-in-part of application No. 12/751,897, filed on Mar. 31, 2010, now Pat. No. 8,439,976.

(60) Provisional application No. 61/414,712, filed on Nov. 17, 2010, provisional application No. 61/165,343, filed on Mar. 31, 2009, provisional application No. 61/168,117, filed on Apr. 9, 2009, provisional application No. 61/259,507, filed on Nov. 9, 2009, provisional application No. 61/311,234, filed on Mar. 5, 2010, provisional application No. 61/311,211, filed on Mar. 5, 2010.

(52) U.S. Cl.
CPC ........... *A61B 2017/0403* (2013.01); *A61B 2017/0404* (2013.01); *A61B 2017/0414* (2013.01); *A61B 2017/06185* (2013.01); *A61F 2/0805* (2013.01); *A61F 2002/087* (2013.01); *A61F 2002/0852* (2013.01); *A61F 2002/0882* (2013.01); *A61F 2210/0057* (2013.01); *A61F 2250/0081* (2013.01); *A61F 2250/0087* (2013.01)

(58) Field of Classification Search
CPC .... A61B 2017/0404; A61B 2017/0403; A61B 2017/0406; A61B 2017/0408; A61B 2017/0409; A61B 2017/0414; A61B 2017/0417; A61B 2017/0419; A61B 2017/042; A61B 2017/0427; A61B 2017/0438; A61B 2017/0445; A61B 2017/0458; A61B 2017/0466; A61B 2017/0496; A61B 2017/06185; A61B 2002/0852; A61B 2002/087
See application file for complete search history.

(56) References Cited

U.S. PATENT DOCUMENTS

| | | |
|---|---|---|
| 4,187,558 A | 2/1980 | Dahlen et al. |
| 4,301,551 A | 11/1981 | Dore et al. |
| 4,400,833 A | 8/1983 | Kurland |
| 4,776,851 A | 10/1988 | Bruchman et al. |
| 4,790,850 A | 12/1988 | Dunn et al. |
| 4,792,336 A | 12/1988 | Hlavacek et al. |
| 4,851,005 A | 7/1989 | Hunt et al. |
| 4,863,471 A | 9/1989 | Mansat |
| 4,917,700 A | 4/1990 | Aikins |
| 4,932,972 A | 6/1990 | Dunn et al. |
| 5,024,669 A | 6/1991 | Peterson et al. |
| 5,026,398 A | 6/1991 | May et al. |
| 5,129,902 A | 7/1992 | Goble et al. |
| 5,171,274 A | 12/1992 | Fluckiger et al. |
| 5,211,647 A | 5/1993 | Schmieding |
| 5,217,495 A | 6/1993 | Kaplan et al. |
| 5,263,984 A | 11/1993 | Li et al. |
| 5,266,075 A | 11/1993 | Clark et al. |
| 5,306,301 A | 4/1994 | Graf et al. |
| 5,320,626 A | 6/1994 | Schmieding |
| 5,397,357 A | 3/1995 | Schmieding et al. |
| 5,540,703 A * | 7/1996 | Barker, Jr. ......... A61B 17/7062 289/1.2 |
| 5,562,669 A | 10/1996 | McGuire |
| 5,575,819 A | 11/1996 | Amis et al. |
| 5,628,756 A | 5/1997 | Barker et al. |
| 5,643,266 A | 7/1997 | Li et al. |
| 5,645,588 A | 7/1997 | Graf et al. |
| 5,699,657 A * | 12/1997 | Paulson ............... B65H 69/06 28/142 |
| 5,931,869 A | 8/1999 | Boucher et al. |
| 5,961,520 A | 10/1999 | Beck, Jr. et al. |
| 5,964,764 A | 10/1999 | West et al. |
| 6,056,752 A | 5/2000 | Roger |
| 6,099,530 A | 8/2000 | Simonian et al. |
| 6,099,568 A | 8/2000 | Simonian et al. |
| 6,110,207 A | 8/2000 | Eichhorn et al. |
| 6,159,234 A | 12/2000 | Bonutti et al. |
| 6,193,754 B1 | 2/2001 | Seedhom |
| 6,203,572 B1 | 3/2001 | Johnson et al. |
| 6,283,996 B1 | 9/2001 | Chervitz et al. |
| 6,296,659 B1 | 10/2001 | Foerster |
| 6,325,804 B1 | 12/2001 | Wenstrom, Jr. et al. |
| 6,517,578 B2 | 2/2003 | Hein |
| 6,533,802 B2 | 3/2003 | Bojarski et al. |
| 7,097,654 B1 | 8/2006 | Freedland |
| 7,494,506 B2 | 2/2009 | Brulez et al. |
| 7,686,838 B2 | 3/2010 | Wolf et al. |
| 7,749,250 B2 | 7/2010 | Stone et al. |
| 7,776,039 B2 | 8/2010 | Bernstein et al. |
| 7,803,173 B2 * | 9/2010 | Burkhart ............ A61B 17/0401 606/228 |
| 7,819,898 B2 | 10/2010 | Stone et al. |
| 7,828,855 B2 | 11/2010 | Ellis et al. |
| 7,875,057 B2 | 1/2011 | Cook et al. |
| 7,905,903 B2 | 3/2011 | Stone et al. |
| 7,914,539 B2 | 3/2011 | Stone et al. |
| 8,109,965 B2 | 2/2012 | Stone et al. |
| 8,118,836 B2 | 2/2012 | Denham et al. |
| 8,162,997 B2 | 4/2012 | Struhl |
| 8,206,446 B1 | 6/2012 | Montgomery |
| 8,231,654 B2 | 7/2012 | Kaiser et al. |
| 2001/0041938 A1 | 11/2001 | Hein |
| 2002/0019649 A1* | 2/2002 | Sikora ............... A61B 17/0401 606/232 |
| 2002/0161439 A1 | 10/2002 | Strobel et al. |
| 2003/0114929 A1 | 6/2003 | Knudsen et al. |
| 2003/0236555 A1* | 12/2003 | Thornes ............. A61B 17/0401 606/232 |
| 2004/0015171 A1 | 1/2004 | Bojarski et al. |
| 2004/0059415 A1 | 3/2004 | Schmieding |
| 2004/0073306 A1 | 4/2004 | Eichhorn et al. |
| 2004/0199166 A1 | 10/2004 | Schmieding et al. |
| 2004/0243235 A1 | 12/2004 | Goh et al. |
| 2004/0267360 A1 | 12/2004 | Huber |
| 2005/0004670 A1 | 1/2005 | Gebhardt et al. |
| 2005/0033363 A1* | 2/2005 | Bojarski ............. A61B 17/0401 606/228 |
| 2005/0065533 A1 | 3/2005 | Magen et al. |
| 2005/0070906 A1 | 3/2005 | Clark et al. |
| 2005/0137624 A1* | 6/2005 | Fallman ............. A61B 17/0057 606/213 |
| 2005/0137704 A1 | 6/2005 | Steenlage |
| 2005/0149187 A1 | 7/2005 | Clark et al. |
| 2005/0171603 A1 | 8/2005 | Justin et al. |
| 2005/0203623 A1 | 9/2005 | Steiner et al. |
| 2005/0261766 A1 | 11/2005 | Chervitz et al. |
| 2006/0052795 A1* | 3/2006 | White ............... A61B 17/0401 606/102 |
| 2006/0067971 A1 | 3/2006 | Story et al. |
| 2006/0095130 A1 | 5/2006 | Caborn et al. |
| 2006/0142769 A1 | 6/2006 | Collette |
| 2006/0265064 A1 | 11/2006 | Re et al. |
| 2006/0293709 A1* | 12/2006 | Bojarski ............. A61B 17/0401 606/232 |
| 2007/0021839 A1 | 1/2007 | Lowe |
| 2007/0083236 A1 | 4/2007 | Sikora et al. |
| 2007/0118217 A1 | 5/2007 | Brulez |
| 2007/0162123 A1 | 7/2007 | Whittaker et al. |
| 2007/0162125 A1 | 7/2007 | LeBeau et al. |
| 2007/0179531 A1 | 8/2007 | Thornes |
| 2007/0225805 A1 | 9/2007 | Schmieding |
| 2007/0239209 A1 | 10/2007 | Fallman |
| 2007/0239275 A1 | 10/2007 | Willobee |
| 2007/0250163 A1 | 10/2007 | Cassani |

(56) References Cited

U.S. PATENT DOCUMENTS

| | | |
|---|---|---|
| 2007/0270857 A1 | 11/2007 | Lombardo et al. |
| 2008/0046009 A1 | 2/2008 | Albertorio et al. |
| 2008/0082127 A1* | 4/2008 | Stone .............. A61B 17/0401 606/232 |
| 2008/0082128 A1* | 4/2008 | Stone .............. A61B 17/0401 606/232 |
| 2008/0177302 A1 | 7/2008 | Shurnas |
| 2008/0188935 A1* | 8/2008 | Saylor .............. A61B 17/0401 623/13.14 |
| 2008/0188936 A1 | 8/2008 | Ball et al. |
| 2008/0208252 A1 | 8/2008 | Holmes |
| 2008/0215150 A1 | 9/2008 | Koob et al. |
| 2008/0228271 A1 | 9/2008 | Stone et al. |
| 2008/0234819 A1 | 9/2008 | Schmieding et al. |
| 2008/0243248 A1 | 10/2008 | Stone et al. |
| 2008/0275553 A1 | 11/2008 | Wolf et al. |
| 2008/0275554 A1 | 11/2008 | Iannarone et al. |
| 2008/0300683 A1 | 12/2008 | Altman et al. |
| 2008/0312689 A1 | 12/2008 | Denham et al. |
| 2009/0018654 A1 | 1/2009 | Schmieding et al. |
| 2009/0030516 A1 | 1/2009 | Imbert |
| 2009/0054982 A1 | 2/2009 | Cimino |
| 2009/0062854 A1 | 3/2009 | Kaiser et al. |
| 2009/0082805 A1* | 3/2009 | Kaiser .............. A61B 17/0401 606/228 |
| 2009/0187244 A1 | 7/2009 | Dross |
| 2009/0216326 A1 | 8/2009 | Hirpara et al. |
| 2009/0228017 A1 | 9/2009 | Collins |
| 2009/0234451 A1 | 9/2009 | Manderson |
| 2009/0265003 A1 | 10/2009 | Re et al. |
| 2009/0275950 A1 | 11/2009 | Sterrett et al. |
| 2009/0306776 A1 | 12/2009 | Murray |
| 2009/0306784 A1 | 12/2009 | Blum |
| 2009/0312776 A1* | 12/2009 | Kaiser .............. A61B 17/0401 606/148 |
| 2010/0049258 A1 | 2/2010 | Dougherty |
| 2010/0049319 A1 | 2/2010 | Dougherty |
| 2010/0100182 A1 | 4/2010 | Barnes et al. |
| 2010/0145384 A1 | 6/2010 | Stone et al. |
| 2010/0145448 A1 | 6/2010 | Montes De Oca Balderas et al. |
| 2010/0152752 A1* | 6/2010 | Denove .............. A61B 17/06066 606/148 |
| 2010/0198192 A1* | 8/2010 | Serina .............. A61B 1/00078 604/523 |
| 2010/0211075 A1 | 8/2010 | Stone |
| 2010/0211173 A1 | 8/2010 | Bardos et al. |
| 2010/0249930 A1 | 9/2010 | Myers |
| 2010/0256677 A1* | 10/2010 | Albertorio .......... A61B 17/0401 606/232 |
| 2010/0268273 A1* | 10/2010 | Albertorio .......... A61B 17/0401 606/232 |
| 2010/0268275 A1 | 10/2010 | Stone et al. |
| 2010/0274355 A1 | 10/2010 | McGuire et al. |
| 2010/0274356 A1 | 10/2010 | Fening et al. |
| 2010/0292792 A1* | 11/2010 | Stone .............. A61B 17/0401 623/13.14 |
| 2010/0305709 A1 | 12/2010 | Metzger et al. |
| 2010/0312341 A1 | 12/2010 | Kaiser et al. |
| 2010/0318188 A1 | 12/2010 | Linares |
| 2010/0324676 A1 | 12/2010 | Albertorio et al. |
| 2010/0331975 A1 | 12/2010 | Nissan et al. |
| 2011/0040380 A1 | 2/2011 | Schmieding et al. |
| 2011/0046734 A1 | 2/2011 | Tobis et al. |
| 2011/0054609 A1 | 3/2011 | Cook et al. |
| 2011/0087280 A1* | 4/2011 | Albertorio ......... A61B 17/0401 606/232 |
| 2011/0087284 A1 | 4/2011 | Stone et al. |
| 2011/0098727 A1* | 4/2011 | Kaiser .............. A61B 17/0401 606/144 |
| 2011/0112640 A1 | 5/2011 | Amis et al. |
| 2011/0112641 A1 | 5/2011 | Justin et al. |
| 2011/0118838 A1 | 5/2011 | Delli-Santi et al. |
| 2011/0137416 A1 | 6/2011 | Myers |
| 2011/0184227 A1 | 7/2011 | Altman et al. |
| 2011/0196432 A1 | 8/2011 | Griffis, III |
| 2011/0196490 A1 | 8/2011 | Gadikota et al. |
| 2011/0218625 A1 | 9/2011 | Berelsman et al. |
| 2011/0238179 A1 | 9/2011 | Laurencin et al. |
| 2011/0270278 A1 | 11/2011 | Overes et al. |
| 2011/0276137 A1 | 11/2011 | Seedhom et al. |
| 2011/0288635 A1 | 11/2011 | Miller et al. |
| 2011/0301707 A1 | 12/2011 | Buskirk et al. |
| 2011/0301708 A1 | 12/2011 | Stone et al. |
| 2012/0046746 A1 | 2/2012 | Konicek |
| 2012/0046747 A1 | 2/2012 | Justin et al. |
| 2012/0053630 A1 | 3/2012 | Denham et al. |
| 2012/0089143 A1 | 4/2012 | Martin et al. |
| 2012/0109299 A1 | 5/2012 | Li et al. |
| 2012/0123474 A1 | 5/2012 | Zajac et al. |
| 2012/0123541 A1 | 5/2012 | Albertorio et al. |
| 2012/0150297 A1 | 6/2012 | Denham et al. |
| 2012/0165938 A1 | 6/2012 | Denham et al. |
| 2012/0197271 A1 | 8/2012 | Astorino et al. |
| 2012/0296345 A1 | 11/2012 | Wack et al. |
| 2013/0023928 A1 | 1/2013 | Dreyfuss |
| 2013/0023929 A1 | 1/2013 | Sullivan et al. |

FOREIGN PATENT DOCUMENTS

| | | |
|---|---|---|
| EP | 0440991 A1 | 8/1991 |
| EP | 1108401 A1 | 6/2001 |
| EP | 1707127 A1 | 10/2006 |
| EP | 2238944 A2 | 10/2010 |
| WO | 2007002561 A1 | 1/2007 |
| WO | 2008091690 A1 | 7/2008 |

* cited by examiner

ADJUSTABLE SUTURE-BUTTON CONSTRUCT FOR KNOTLESS STABILIZATION OF CRANIAL CRUCIATE DEFICIENT LIGAMENT STIFLE

CROSS-REFERENCE TO RELATED APPLICATIONS

This application is a continuation of U.S. application Ser. No. 14/089,097, filed Nov. 25, 2013, now U.S. Pat. No. 9,421,086,which is a divisional of U.S. application Ser. No. 13/298,912, filed Nov. 17, 2011, now U.S. Pat. No. 8,628, 573, which claims the benefit of U.S. Provisional Application No. 61/414,712, filed Nov. 17, 2010, the entire disclosures of which are incorporated by reference herein This application is also a continuation-in-part of U.S. application Ser. No. 12/751,835, filed Mar. 31, 2010, now U.S. Pat. No. 8,460,379 and U.S. application Ser. No. 12/751,897, filed Mar. 31, 2010, now U.S. Pat. No. 8,439, 976, each of which claims the benefit of U.S. Provisional Application No. 61/165,343, filed Mar. 31, 2009, U.S. Provisional Application No. 61/168,117, filed Apr. 9, 2009, U.S. Provisional Application No. 61/259,507, filed Nov. 9, 2009, U.S. Provisional Patent Application No. 61/311,234, filed Mar. 5, 2010, and U.S. Provisional Patent Application No. 61/311,211, filed Mar. 5, 2010, the entire disclosures of which are incorporated by reference herein.

FIELD OF THE INVENTION

The present invention relates to methods and suture/button/needle constructs for ligament repair and, more specifically, for cranial cruciate ligament repair in canines.

BACKGROUND OF THE INVENTION

Cruciate ligament repairs, particularly canine Cranial Cruciate Ligament (CrCL) repairs, involve attachment of the CrCL to the femur (running across the stifle joint) and attachment to the tibia. The CrCL holds the tibia in place and prevents excess anterior drawer, internal rotation and hyperextension. CrCL rupture occurs primarily in the knees of dogs and cats, and is one of the most common orthopedic injuries in dogs. CrCL rupture is also the most common cause of degenerative joint disease in the stifle joint. When a CrCL is torn, it causes sudden pain, instability in the knee joint, and often results in the pet holding its leg up. The pet may put the leg down and start using it within few days, but will continue to limp for several weeks. Typically, at the end of several weeks, the initial pain subsides and the pet will try to use its leg more; however, the joint remains unstable. Every time the animal puts weight on the leg, the tibia slides forward relative to the femur. This abnormal motion causes wear and tear on the joint cartilage, causing pain and leading to arthritis. This motion can also impart excessive stress on the menisci (C-shaped cartilage within the knee joint), causing damage or tearing.

A suture-button construct for stabilization of a cranial cruciate ligament deficient stifle, and associated surgical method, is the subject matter of U.S. Pat. No. 7,875,057, issued on Jan. 25, 2011, the disclosure of which is incorporated by reference herein in its entirety. The construct and associated technique disclosed in this prior patent greatly facilitates CrCL repair as compared to the prior art, but it requires the tying of knots to secure the second button against the medial side of the femur or tibia, depending on orientation of the construct. It also requires either a second incision or an incision large enough that allows exposure of the lateral aspect of the joint and the medial aspect where the knots are being tied to secure the button. A CrCL construct and technique is needed which provides the same repair and fixation as disclosed in the aforementioned patent, but without the need for tying knots or a second incision.

SUMMARY OF THE INVENTION

The present invention provides methods and reconstruction systems (a self-locking, adjustable, knotless button/loop/needle construct) for extracapsular ligament reconstruction in mammals. The reconstruction system comprises a button/loop needle construct formed of a pair of fixation devices (for example, two buttons) connected by flexible loops. At least one of the loops includes a flexible material with two or more adjustable splices/eyesplices that are interconnected to form an adjustable, flexible, continuous, knotless loop. A needle can be attached to each of the fixation devices to guide the respective fixation device through the bone tunnels out of the opposite end.

The fixation devices that emerge from the tunnels are seated against the femoral and tibial cortex. A draw strand of the button/loop construct is pulled to cinch down the construct. After the desired tension is obtained, the extra strands of suture are cut at the tunnel site, and the needles are cut free.

The present invention also provides a method of canine ligament repair and fixation to bone. The method of the present invention comprises inter alia the steps of: (i) providing tibial and femoral tunnels or holes through the tibia and femur; (ii) providing a reconstruction system comprising a knotless button/loop needle construct including two fixation devices (for example, two buttons), at least one flexible, adjustable continuous loop attached to one of the fixation devices (e.g., the buttons), and two needles (each needle being attached to one fixation device, e.g., the button); (iii) securing the construct by advancing the button/loop needle construct through the femoral and tibial tunnels (by using each of the needles as a guide to pull each button), until each button exits the respective tunnel and flips; and (iv) cinching the construct to provide secure seating of each button against the femoral and tibial cortex and stabilization of the joint.

These and other features and advantages of the present invention will become apparent from the following description of the invention that is provided in connection with the accompanying drawings and illustrated embodiments of the invention.

DETAILED DESCRIPTION OF THE INVENTION

The present invention provides surgical procedures and reconstruction systems for the stabilization of the cranial cruciate ligament deficient stifle using a button/loop/needle construct in a minimally invasive approach. The present invention also provides methods and reconstruction systems (a self-locking, adjustable, knotless button/loop/needle construct) for extracapsular ligament reconstruction in mammals.

The reconstruction system of the present invention comprises a knotless button/loop/needle construct including two fixation devices (for example, two buttons), at least one flexible, adjustable loop attached to at least one of the fixation devices (e.g., the buttons), and two needles (each needle being attached to one fixation device, e.g., the button). The knotless button/loop/needle construct has an adjustable loop length and allows adjustment in one direction while preventing or locking the construct from loosening in the opposite direction, due to applied tensile forces. The construct and techniques of the present invention provide an improved knotless system for cruciate ligament repair.

At least one of the loops include a flexible material with two or more adjustable eyesplices/splices that are interconnected to form an adjustable loop. Each needle (attached to each of the buttons) guides the respective button through the bone tunnels out of the opposite end. The buttons that emerge from the tunnels are seated against the femoral and tibial cortex. A draw strand of the suture-button construct is pulled to cinch down the construct. After the desired tension is obtained, the extra strands of suture are cut at the tunnel site, and the needles are cut free.

The present invention also provides a method of canine ligament reconstruction by inter alia: (i) drilling tunnels through the tibia and femur; (ii) providing a button/loop/needle construct with two buttons and at least one flexible, adjustable loop (a four-point knotless fixation device) that is capable of adjusting tension (e.g., is provided with a loop having an adjustable perimeter and length), and with two needles (each needle being attached to one of the buttons); (iii) securing the construct by advancing the button/loop/needle construct through the femoral and tibial tunnels (by using each of the needles as a guide to pull each button) until each button exits the respective tunnel and flips; and (iv) cinching the construct to provide secure seating of each button against the femoral and tibial cortex and stabilization of the joint.

Figure 1:
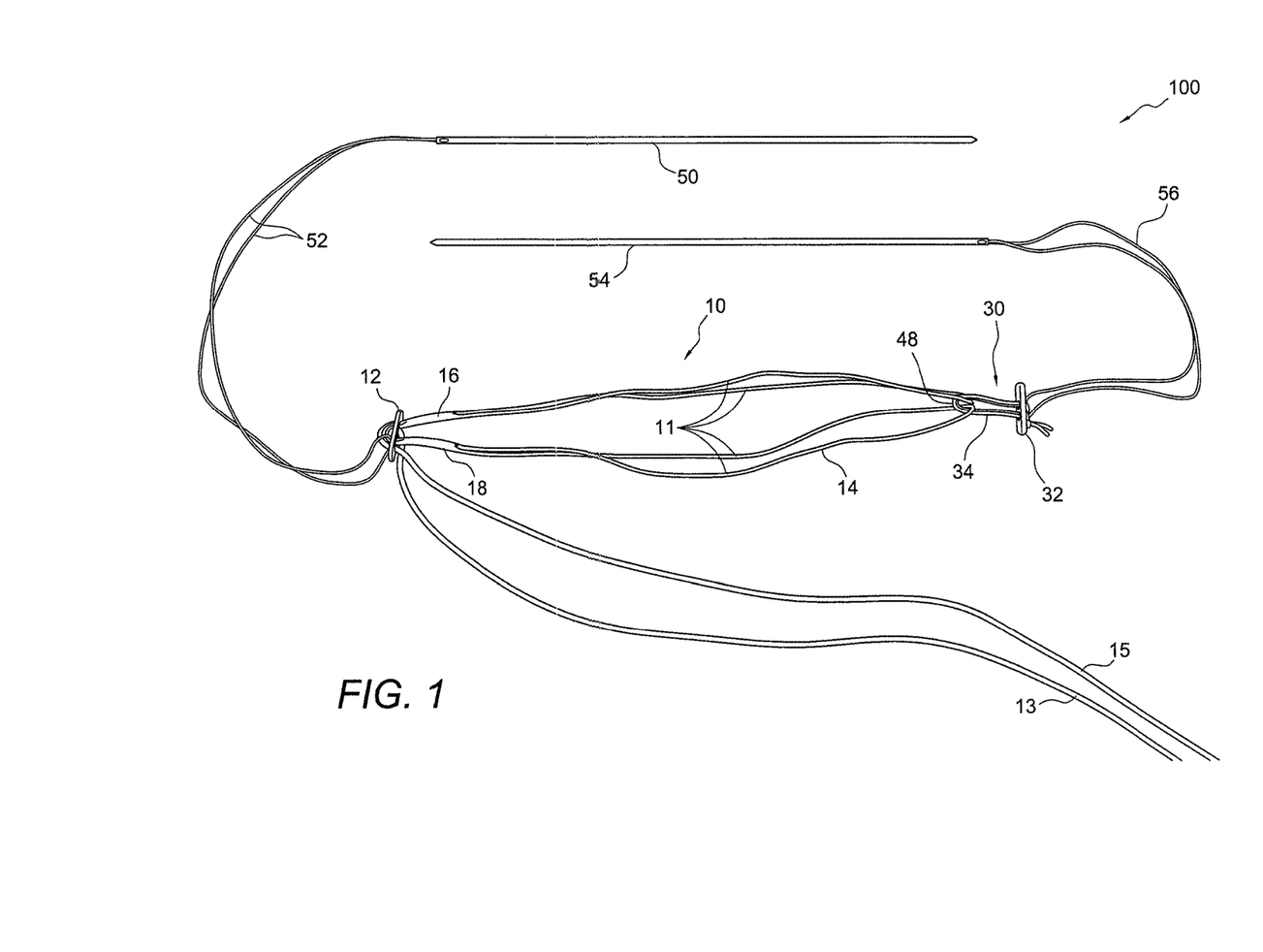
FIG. 1 illustrates an adjustable, knotless button/loop needle construct (with two buttons, two continuous loops, wherein at least one of the two loops is a flexible, adjustable loop, and two needles) according to an exemplary embodiment of the present invention.

Referring now to the drawings, where like elements are designated by like reference numerals, FIG. 1 illustrates an exemplary embodiment of a knotless reconstruction system 100 of the present invention. The reconstruction system 100 is an integrated system comprising (i) two interconnected knotless button/loop constructs each including a fixation device (for example, a button) and at least one flexible, adjustable loop attached to the fixation device (e.g., the button); and (ii) two needles, each needle being attached to a fixation device of the knotless button/loop constructs. FIGS. 2-7 illustrate exemplary steps of a method of cruciate ligament repair with the reconstruction system 100 of FIG. 1.

As shown in FIG. 1, knotless stabilization/reconstruction system 100 comprises two button/loop/needle constructs 10, 30 formed by a pair of fixation devices 12, 32 connected by flexible, adjustable loops 14, 34. At least one of the loops 14, 34 includes a flexible material 11 with two or more adjustable splices/eyesplices 16, 18 that are interconnected to form the adjustable loop. Two needles 50, 54 are attached to each fixation device (through passing suture 52 and 56, respectively) so that each of the needle guides the respective fixation device 12, 32 through the bone tunnels out of the opposite end.

In an exemplary and illustrative embodiment only, the fixation devices are buttons having a similar or different configuration. The buttons may have a body with an oblong, elongate configuration, to allow passage of the buttons through tibia and femoral tunnels. Although the embodiments below will be detailed with reference to particular configurations for the first and second fixation devices 12, 32 (e.g., two narrow, oblong, elongate buttons), the invention is not limited to this exemplary embodiment only and has applicability to fixation devices with other shapes and geometries, as long as the fixation devices are provided with apertures/holes/passages that allow a flexible material (a flexible strand) to pass therethrough (or be threaded therethrough) to form the flexible, adjustable, self-cinching, knotless loops of the invention.

The flexible material 11 forming the interconnected loops has an adjustable length and, as described below, is connected to two fixation devices (buttons) 12, 32 that are further secured on tibial cortex and fibular cortex, respectively. The flexible material 11 is threaded through apertures/holes/eyelets of each of the first and second fixation devices 12, 32 and splices are created to form the knotless, integrated, self-cinching reconstruction system 100. In an exemplary only embodiment, and as detailed below, the flexible material 11 may be suture such as a suture braid with braided filaments having a hollow core (for example, strands of suture such as ultrahigh molecular weight polyethylene (UHMWPE) braided with strands of polyester, collagen, or other suture materials, such as PET, PEEK, silk nylon, and absorbable polymers, among many others).

In an exemplary and illustrative embodiment only, self-locking button/loop/needle construct 10 includes a button 12 and flexible material 11 with two or more adjustable eyesplices 16, 18 that are interconnected to form one adjustable loop 14. By pulling on free braid strands 13, 15, the individual eyesplices 16, 18 constrict and, in turn, reduce the loop length of loop 14. Elongation of the construct is constricted because, in order for loop 14 to elongate, a force must be applied interior to one or both of the eyesplices 16, 18. Although FIG. 1 illustrates an exemplary embodiment with an adjustable loop having two eyesplices 16, 18, the invention is not limited to this exemplary only embodiment and also contemplates embodiments with more than two eyesplices, e.g., with more splicing points which will confer additional strength to the self-locking button/loop construct replacing the canine ligament.

Details regarding the formation/assembly of a self-locking adjustable construct with one fixation device and two adjustable splices (and which allows, for example, a graft to be fully inserted and seated in a bone tunnel) are provided in U.S. Patent Application Publication Nos. 2010/0256677 and 2010/0268273, the disclosures of which are incorporated by reference in their entirety herewith.

As described in the above-noted applications, a self-locking, adjustable, knotless construct includes a button and a flexible material with two adjustable eyesplices that are interconnected to form an adjustable continuous loop. By pulling on the free braid strands, the individual eyesplices constrict and, in turn, reduce the loop length L of loop. In order for the loop to elongate, a force needs to be applied interior to one or both of the eyesplices to elongate the individual loops.

Exemplary steps of a method of forming/assembling a self-locking, adjustable knotless construct 10 with one fixation device (e.g., one button) and two splices/eyesplices are detailed in the above-noted applications, and include as starting materials a suture strand (for example, 50 inches of braided UHMWPE strand); a needle (for example, a blunt tip needle with nitinol loop) and a button (for example, a 3.5 mm titanium button). The suture strand is folded to create two equal length parallel braid strands. At this step, the braid is folded at the midpoint, 25 inches, to create two parallel equal length braid strands (Step 1). At Step 2, a first eyesplice is created on the first strand of braid by passing the blunt tip needle through the center of the braid with the end of the braid being carried through in the nitinol loop of the needle. In one embodiment, the splice should travel for a distance of about 17-19 mm through the braid towards the braid midpoint created in Step 1. In another embodiment, the splice should travel for a distance of about 25 mm.

Once the first eyesplice has been formed, at Step 3, the button is slid over the non-spliced strand passing the strand through both button holes. The button is slid so that it rests over the first spliced section. At Step 4, a second eyesplice is formed, similar to the first one, with the opposing strand. The strand is looped through the first eyesplice loop, resulting in two eyesplice loops that are interconnected. Again, as detailed above, the splice length is about between 17-19 mm, or about 25 mm. The splice should be created such that the exiting aperture of the splice is as close as possible to the first eyesplice. FIG. 1 also shows two splice entrance points 16, 18 of the self-locking button/loop needle construct 10. For embodiments contemplating more than two eyesplices for the self-locking button/loop needle construct, there will be an according number of corresponding splice entrance points.

According to an exemplary and illustrative embodiment only, self-locking, knotless button/loop/needle construct 30 may be formed similarly to the construct 10 (as detailed above) or may be formed by connecting a flexible loop 34 of flexible material to a fixation device such as button 32. Either way, loop 34 interconnects with loop 14, as shown in FIG. 1 (i.e., loop 34 is looped over loop 14 during the assembling). Loop 34 may also have an adjustable length/perimeter and may be provided with any number of eyesplices.

Buttons 12, 32 of the construct 100 may be formed, for example, of metal, PEEK or PLLA. Details of buttons 12, 32 are also set forth in U.S. Patent Publ. No. 2007/0179531 (Thornes). As detailed in U.S. Patent Publ. No. 2007/0179531, buttons 12, 32 are provided with a plurality of holes that allows the flexible material (preferably suture, as described below) to pass thereto. Each of buttons 12, 32 may be preferably oblong and may be provided with two or more apertures.

In additional embodiments, at least one of the buttons 12, 32 may be also a narrow button with at least one lateral hole (a hole on the end of the button) for secure engagement of the button to an inserter instrument, as described and detailed in U.S. Patent Publ. No. 2009/0105754, the disclosure of which is incorporated in its entirety herewith. As described in U.S. Patent Publ. No. 2009/0105754, the narrow button is provided with one or more inside eyelets (for example, a right eyelet or hole, and a left eyelet or hole) that allow the passage of the suture, and also with at least one lateral hole which allows engagement of the button to an inserter instrument (such as a button inserter or applicator that comprises a shaft, a handle, an inner rod, a bolt, a slide, a spring and a cap).

The flexible material 11 of the adjustable loops is preferably a braided high strength suture material, such as a suture formed of braided strands of ultrahigh molecular weight polyethylene. The braided high strength suture may be provided with optional colored strands to assist surgeons in distinguishing between suture lengths with the trace and suture lengths without the trace.

The knotless repair system 100 of the present invention may be employed in a method of stabilization of a cranial cruciate ligament deficient stifle, for example, which is accomplished without tying knots. In one embodiment, the tibial hole is drilled in the tibia by entering the tibia on the lateral side just distal to the articular margin of the proximal tibia and within the extensor groove underneath the LDE tendon and exiting the tibia on a medial side. Once the tibial and femoral tunnels/holes have been drilled through the tibia and femur, the knotless construct 100 of the present invention is secured to the tunnels/holes by advancing the construct through the femoral and tibial tunnels (by using each of the needles as a guide to pull each button) until each button exits the respective tunnel and flips. Cinching of the construct provides secure seating of each button against the femoral and tibial cortex and stabilization of the joint.

According to an exemplary embodiment, the tissue to be treated is a canine CrCL. FIGS. 2-7 illustrate a canine knee 90 in a lateral perspective undergoing a method of CrCL reconstruction using construct 100 of FIG. 1 according to the present invention. Also shown in FIGS. 2-7 are femur 91, tibia 93 and damaged ligament 95.

The joint is first explored and preparation of the knee cavity is conducted by removing any remaining articular cartilage using a combination of a rasp, curette and mechanical burr, for example. The canine is positioned in lateral or dorsal recumbency preferably under general anesthetic and prepared for surgery of the affected stifle. A hanging limb technique with aseptic preparation and appropriate draping may be performed. A lateral parapatellar approach with arthrotomy may be performed and complete exploration of the stifle joint may be conducted. The joint capsule is closed and tibial tunnel 93a and femoral tunnel 91a are created at the appropriate locations in the proximal tibia 93 and femur 91, for tibial and femoral fixation.

Figure 2:
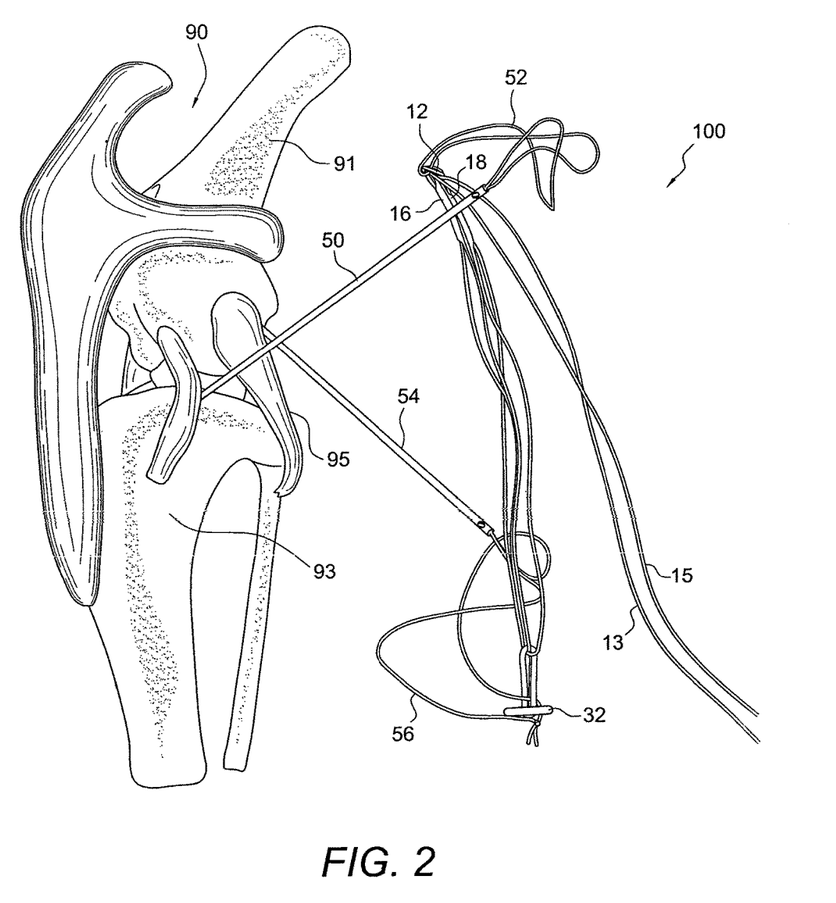
FIGS. 2-7 illustrate exemplary steps of a method of CrCL reconstruction on a canine knee and with the adjustable, knotless button/loop needle construct of FIG. 1, and according to an exemplary embodiment of the present invention.
Figure 3:
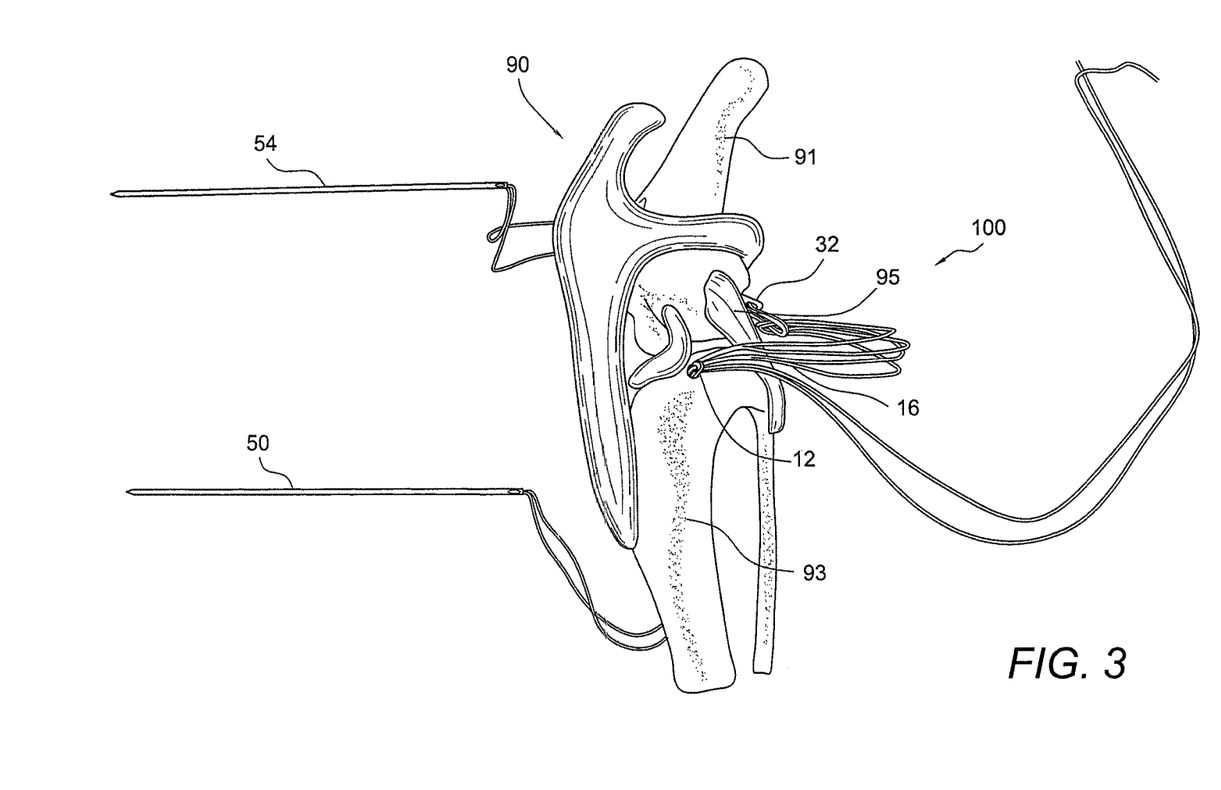

After creation of the femoral and tibial bone tunnels 91a, 93a, each needle 50, 54 is guided through the tunnel (FIG. 2). The draw string that cinches down the construct 10 is left on the lateral side of the joint (FIG. 2). FIG. 3 illustrates needles 50, 54 pushed through the skin after leaving the bone tunnel. The needles are used to guide corresponding buttons 12, 32 through a respective bone tunnel 91a, 93a in the tibia and femur, illustrated in FIG. 6.

Figure 4:
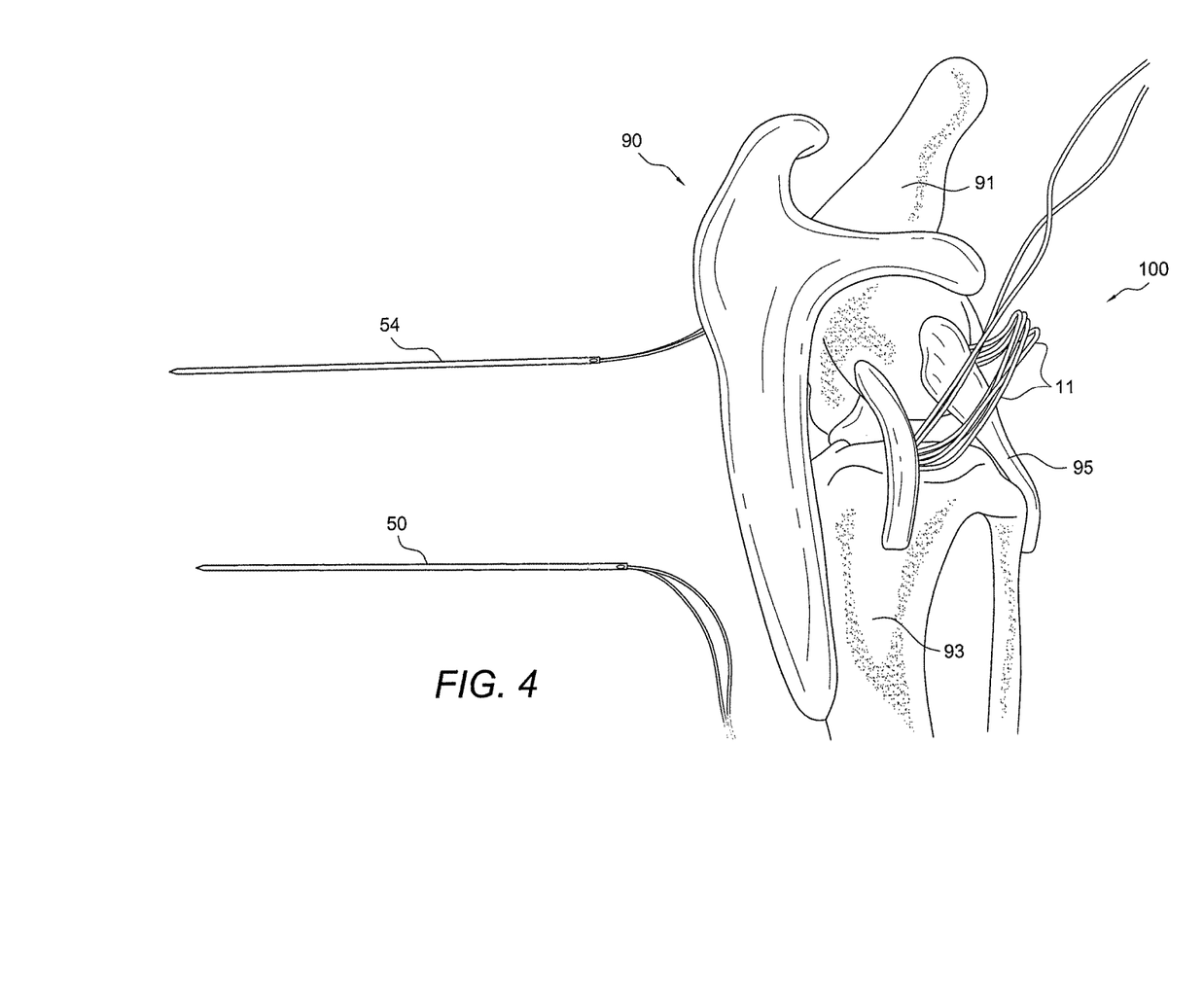

FIG. 4 illustrates the buttons 12, 32 pulled through the tibial and femoral tunnels 91a, 93a, respectively. The loops associated with the construct 10 are on the lateral side, and the cinching part of the construct 100 is also left on the lateral side of the joint.

Figure 5:
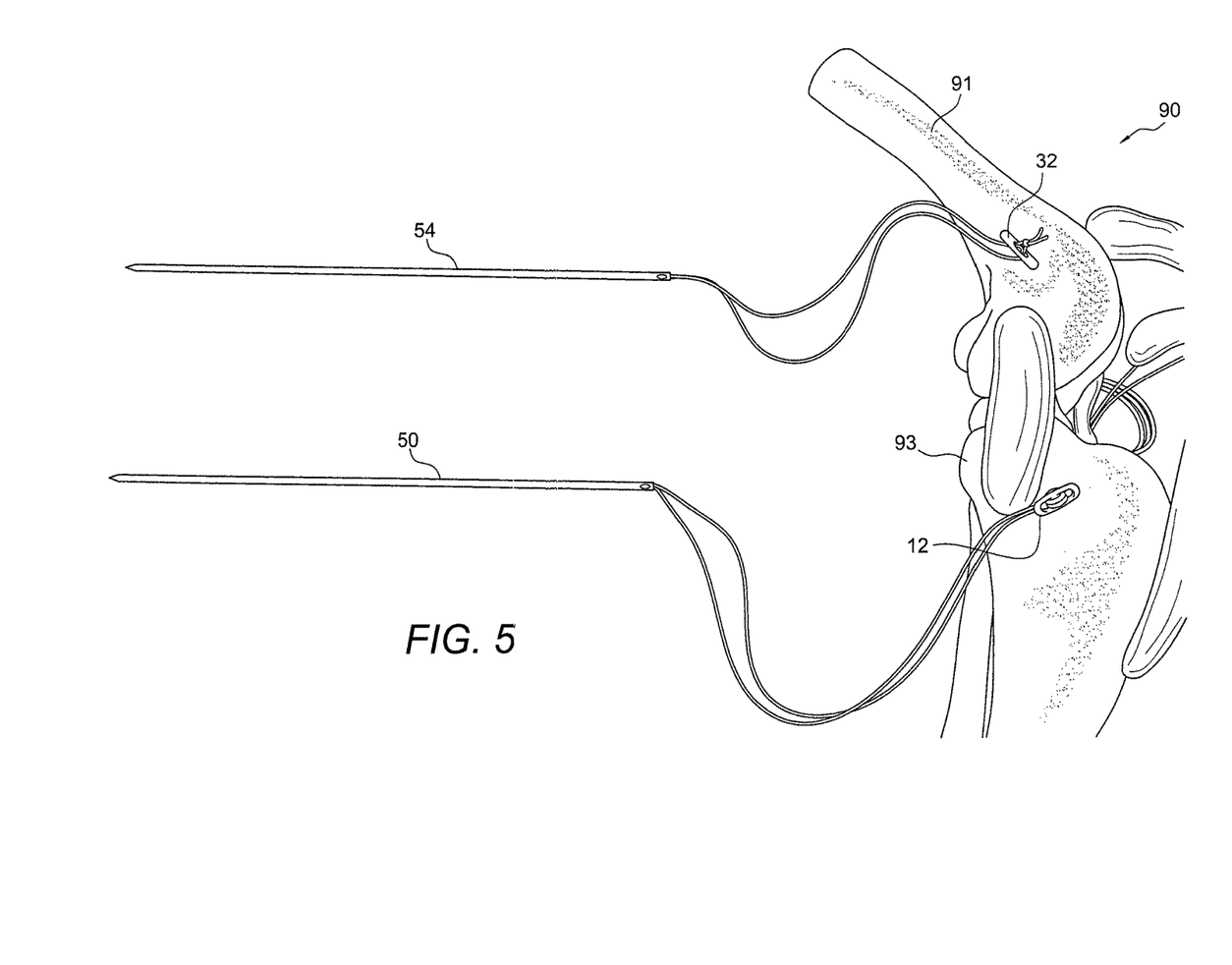

FIG. 5 shows the medial side with the buttons 12, 32 seated against the femoral and tibial cortex.

Figure 6:
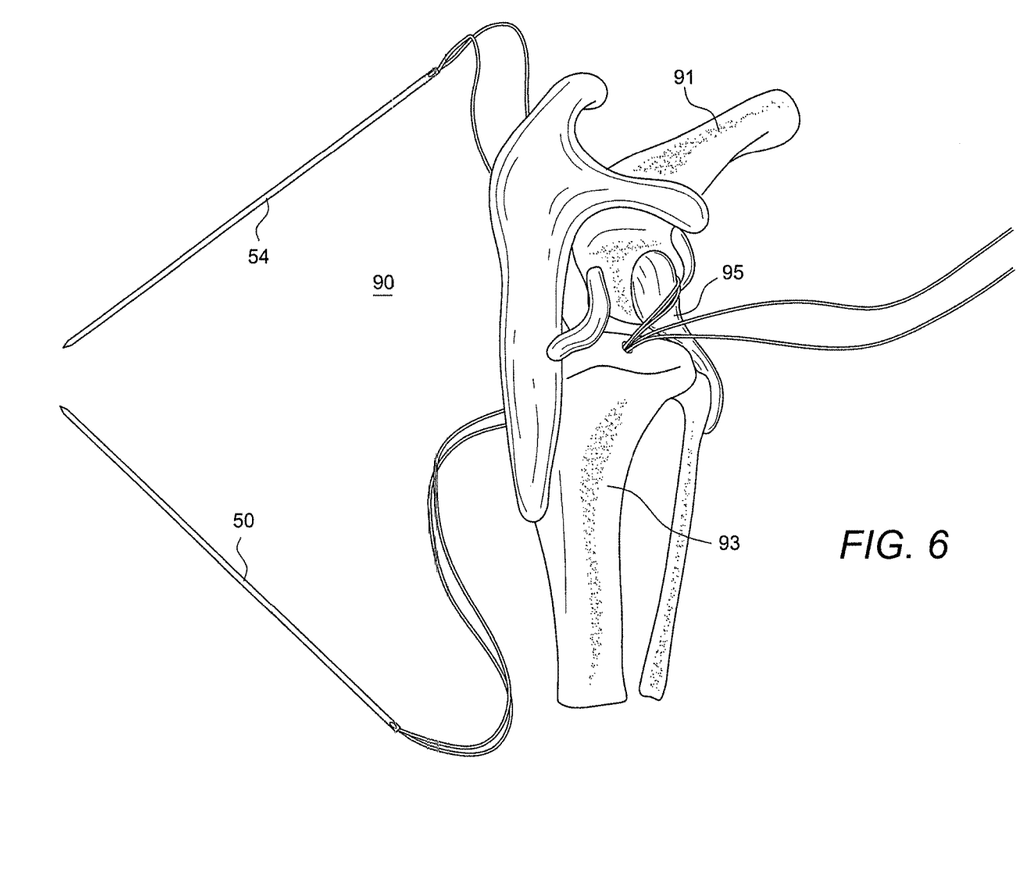

FIG. 6 illustrates how the cinching part of the structure 100 is tightened to apply tension through the construct.

Figure 7:
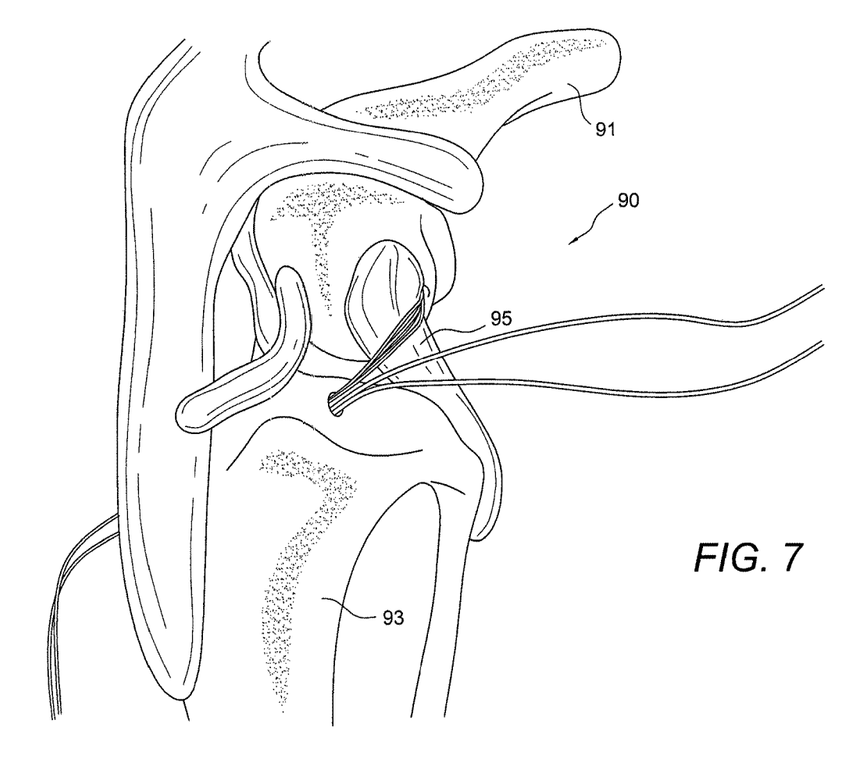

Once the desired tension is obtained, the extra strands of suture can be cut at the tunnel site, and the needles 50, 54 can be cut free, as shown in FIG. 7.

The flexible material 11 forming the adjustable, knotless loops is preferably a braided high strength suture material, such as described in U.S. Pat. No. 6,716,234, the disclosure of which is incorporated by reference. The flexible material 11 may be provided with optional colored strands to assist surgeons in distinguishing between suture lengths with the trace and suture lengths without the trace. The flexible material 11 may be also provided in the form of a suture tape, or a combination of suture strand and suture tape, and as desired. The flexible material 11 may be suture such as such as a suture braid with braided filaments having a hollow core (for example, strands of suture such as ultrahigh molecular weight polyethylene (UHMWPE) braided with strands of polyester, collagen, or other suture materials, such as PET, PEEK, silk nylon, and absorbable polymers, among many others). The flexible material 11 may also contain a bioabsorbable material, such as PLLA or one of the other polylactides, for example, and/or may be formed of twisted fibers having strands of a contrasting color added to the braided threads, to make the suture more visible during surgical procedures. In exemplary embodiments, flexible material may be a braided suture cover containing strands of a high strength suture material, such as FiberWire™ suture, sold by Arthrex, Inc. of Naples, Fla.

Buttons 12, 32 of the construct 100 of the present invention may be formed, for example, of metal, PEEK or PLLA. As detailed above, the buttons are provided with openings (apertures, eyelets, holes) that allow the passage of the flexible material to pass thereto.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed is:

1. A knotless reconstruction system, comprising:
a first fixation device;
a first flexible, adjustable loop connected to the first fixation device;
a second fixation device;
a second flexible, adjustable loop connected to the second fixation device and interconnected with the first flexible, adjustable loop;
a first passing suture connected to the first fixation device and a second passing suture connected to the second fixation device; and
a first needle connected to the first passing suture and a second needle attached to the second passing suture.

2. The knotless reconstruction system as recited in claim 1, wherein the first flexible, adjustable loop includes a first adjustable eyesplice and a second adjustable eyesplice interconnected with the first adjustable eyesplice.

3. The knotless reconstruction system as recited in claim 2, comprising a free braid strand that extends from at least one of the first adjustable eyesplice and the second adjustable eyesplice.

4. The knotless reconstruction system as recited in claim 3, wherein the free braid strand is movable to constrict at least one of the first adjustable eyesplice and the second adjustable eyesplice.

5. The knotless reconstruction system as recited in claim 1, wherein the second flexible, adjustable loop is looped over the first flexible, adjustable loop.

6. The knotless reconstruction system as recited in claim 1, wherein the second flexible, adjustable loop is interconnected with the first flexible, adjustable loop prior to connecting the second flexible, adjustable loop to the second fixation device.

7. The knotless reconstruction system as recited in claim 1, wherein the first fixation device is a first button having a first configuration and the second fixation device is a second button having a second, different configuration.

8. The knotless reconstruction system as recited in claim 7, wherein at least one of the first button and the second button includes a lateral hole adapted to receive an inserter instrument.

9. A cranial cruciate ligament repair system, comprising:
a first button/loop construct having a first button and a first adjustable loop connected to the first button;
a second button/loop construct having a second button and a second adjustable loop connected to the second button;
wherein the first adjustable loop and the second adjustable loop are connected to each other, and at least one of the first adjustable loop and the second adjustable loop is a self-cinching knotless loop having an adjustable length and includes at least two interconnected eyesplices; and
wherein an un-spliced section of the self-cinching knotless loop extends between the at least two interconnected eyesplices and is received by the first button or the second button.

10. The system as recited in claim 9, wherein the first button/loop construct includes a first passing suture attached to the first button and the second button/loop construct includes a second passing suture attached to the second button.

11. The system as recited in claim 9, wherein the at least one of the first adjustable loop and the second adjustable loop includes a free braid strand movable to alter the adjustable length.

12. The system as recited in claim 9, wherein the first button and the second button each include an oblong body having at least two apertures.

13. The system as recited in claim 9, wherein the at least two interconnected eyesplices includes a first adjustable eyesplice and a second adjustable eyesplice interconnected with the first adjustable eyesplice, and the second adjustable loop includes a third adjustable eyesplice and a fourth adjustable eyesplice interconnected with the third adjustable eyesplice.

14. The system as recited in claim 13, wherein the second adjustable loop is looped over the first adjustable loop.

15. The system as recited in claim 13, comprising a first free braid strand that extends from the first adjustable eyesplice, a second free braid strand that extends from the second adjustable eyesplice, a third free braid strand that extends from the third adjustable eyesplice, and a fourth free braid strand that extends from the fourth adjustable eyesplice.

16. The system as recited in claim 13, wherein a first filament forming the first adjustable eyesplice is received through an opening established by a looped portion of the second adjustable eyesplice to interconnect the first adjustable eyesplice and the second adjustable eyesplice.

17. The system as recited in claim 9, wherein the first adjustable loop includes the at least two interconnected eyesplices, and the second adjustable loop is separate from either of the at least two interconnected eyesplices.

18. The system as recited in claim 9, wherein the first adjustable loop includes:
a first adjustable eyesplice; and
a first free braid strand extending from the first adjustable eyesplice and being movable to adjust a size of the first adjustable loop,
wherein the first free braid strand passes from the first adjustable eyesplice through an opening of the first button.

19. A cranial cruciate ligament repair system, comprising:
a first button/loop construct having a first button and a first adjustable loop connected to the first button;
a second button/loop construct having a second button and a second adjustable loop connected to the second button,
wherein the first adjustable loop and the second adjustable loop are connected to each other, and at least one of the first adjustable loop and the second adjustable loop is a self-cinching knotless loop having an adjustable length and includes at least two interconnected eyesplices;
a first passing suture attached to the first button and the second button/loop construct includes a second passing suture attached to the second button; and
a first needle attached to the first passing suture and a second needle attached to the second passing suture.

\* \* \* \* \*